United States Patent [19]

Granger et al.

[11] Patent Number: 5,306,288
[45] Date of Patent: Apr. 26, 1994

[54] COMBINED SURGICAL NEEDLE-SUTURE DEVICE

[75] Inventors: Richard N. Granger, Huntington; Michael S. Kassim, Monroe, both of Conn.

[73] Assignee: United States Surgical Corporation, Norwalk, Conn.

[21] Appl. No.: 693,441

[22] Filed: Apr. 29, 1991

Related U.S. Application Data

[63] Continuation-in-part of Ser. No. 670,992, Mar. 18, 1991, abandoned, which is a continuation-in-part of Ser. No. 576,046, Sep. 5, 1990, abandoned.

[51] Int. Cl.$^5$ .............................................. A61B 17/00
[52] U.S. Cl. ................................. 606/227; 606/224; 606/225; 606/226
[58] Field of Search .......... 606/227, 226, 223, 224–226

[56] References Cited

U.S. PATENT DOCUMENTS

| | | |
|---|---|---|
| 86,769 | 2/1869 | Marriott . |
| 295,612 | 3/1884 | Bailey . |
| 299,305 | 5/1904 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar . |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. . |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,701 | 7/1968 | Dery . |
| 3,416,534 | 12/1968 | Quinn ............................ 128/418 |
| 3,799,169 | 3/1974 | Beroff et al. . |
| 3,835,912 | 9/1974 | Kristensen et al. . |
| 3,875,946 | 4/1975 | Duncan . |
| 3,880,167 | 4/1975 | Hardwick . |
| 3,890,975 | 6/1975 | McGregor . |
| 3,910,232 | 10/1975 | Messer et al. . |
| 3,918,455 | 11/1975 | Coplan . |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1978 | Hunter . |
| 3,980,177 | 9/1976 | McGregor . |
| 3,981,307 | 9/1976 | Borysko . |
| 3,981,307 | 9/1976 | Borysko . |
| 4,054,144 | 10/1977 | Hoffman et al. . |
| 4,072,041 | 2/1970 | Hoffman et al. ................. 72/416 |
| 4,124,027 | 11/1970 | Boss . |
| 4,127,133 | 11/1978 | Martinez . |
| 4,169,477 | 10/1979 | Bokros ............................... 29/447 |
| 4,359,053 | 11/1982 | Benjamin . |
| 4,411,654 | 10/1983 | Boarini et al. ...................... 604/165 |
| 4,596,728 | 6/1986 | Yang et al. ......................... 428/36 |
| 4,624,879 | 11/1986 | Van Dijck et al. ............ 1.428/102 |
| 4,672,734 | 6/1987 | Kawada et al. ................... 29/517 |
| 4,792,336 | 12/1988 | Hlavacek et al. ................. 623/13 |
| 4,805,292 | 2/1989 | Noguchi ............................ 29/445 |
| 4,926,860 | 5/1990 | Stice et al. ........................ 606/144 |

FOREIGN PATENT DOCUMENTS

| | | |
|---|---|---|
| 0358451 | 3/1980 | European Pat. Off. . |
| 9101152.3 | 5/1991 | Fed. Rep. of Germany . |
| 2432861 | 1/1974 | France . |

OTHER PUBLICATIONS

Raychem RT-850 Product Specification.

*Primary Examiner*—Stephen C. Pellegrino
*Assistant Examiner*—Gary Jackson

[57] ABSTRACT

A combined surgical needle-suture device is provided by attaching the reduced shank of a needle and the tip region of a suture to each other through a heat shrinkable tubing fitted around both, the axial length of the tubing bearing a defined relationship to the effective axial length of the needle shank. In the preferred detachable needle-suture device, a removal interface having a predetermined axial length and/or contact area is defined between a shrinkable tubing having a predetermined axial length and a suture tip region.

57 Claims, 3 Drawing Sheets

COMBINED SURGICAL NEEDLE-SUTURE DEVICE

This is a continuation-in-part of copending application Ser. No. 07/670,992, filed Mar. 18, 1991, now abandoned, which is a continuation-in-part of Ser. No. 07/576,046, filed Sep. 5, 1990, now abandoned.

BACKGROUND OF THE INVENTION

The present invention relates to a combined surgical needle-suture device and, more particularly, to such a device in which a shrinkable tubing attaches a suture to a surgical needle.

For many years, surgeons have employed needle-suture combinations in which the tip of the suture or ligature is attached to the blunt, or shank, end of the needle. Such needle-suture combinations are provided for a wide variety of monofilament and braided suture materials, e.g., nonabsorbable materials such as surgical gut, silk, nylon, polyester, polypropylene, linen and cotton, and absorbable materials such as the synthetic polymers and copolymers of glycolic and lactic acids.

Needle-suture combinations fall into two general classes: standard needle-suture devices and standard detachable needle-suture devices. In the case of standard needle-suture devices, the suture is securely attached to the needle and is not intended to be separable therefrom except by a deliberate cutting or severing of the suture. By contrast, in standard detachable needle-suture devices, separation of the needle from the suture is achieved by application of a separation, or pull-out, force applied by the surgeon. Minimum acceptable pull-out forces required to separate a needle from a suture (for various suture sizes) are set forth in the *United States Pharmacopeia* (USP). The *United States Pharmacopeia* prescribes minimum individual pull-out forces and minimum average pull-out forces as measured for five needle-suture combinations. The minimum pull-out forces for both standard and removable needle-suture attachment set forth in the USP are hereby incorporated by reference and are as follows.

| Standard Needle Attachment for Absorbable And Nonabsorbable Sutures | | | | |
|---|---|---|---|---|
| Metric Size (Gauge No.) | | | Limits on Needle Attachment | |
| Absorbable (Collagen) Suture | Nonabsorbable and Synthetic Absorbable Suture | UPS Size | Average (kgf) (Min.) | Individual (kgf) (Min.) |
|  | 0.1 | 11-0 | 0.007 | 0.005 |
|  | 0.2 | 10-0 | 0.014 | 0.010 |
| 0.4 | 0.3 | 9-0 | 0.021 | 0.015 |
| 0.5 | 0.4 | 8-0 | 0.050 | 0.025 |
| 0.7 | 0.5 | 7-0 | 0.080 | 0.040 |
| 1 | 0.7 | 6-0 | 0.17 | 0.08 |
| 1.5 | 1 | 5-0 | 0.23 | 0.11 |
| 2 | 1.5 | 4-0 | 0.45 | 0.23 |
| 3 | 2 | 3-0 | 0.68 | 0.34 |
| 3.5 | 3 | 2-0 | 1.10 | 0.45 |
| 4 | 3.5 | 0 | 1.50 | 0.45 |
| 5 | 4 | 1 | 1.80 | 0.60 |
| 6 & larger | 5 & larger | 2 & larger | 1.80 | 0.70 |

The requirements are met if neither the average of 5 values nor any individual value is less than the limit given in the foregoing table.

| Removable Needle Attachment for Absorbable and Nonabsorbable Sutures | | | | |
|---|---|---|---|---|
| Metric Size (Gauge No.) | | | Attachment Limits | |
| Absorbable (Collagen) | Nonabsorbable and Synthetic Absorbable | USP Size | Minimum (kgf) | Maximum (kgf) |
| 1.5 | 1 | 5-0 | 0.028 | 1.59 |
| 2 | 1.5 | 4-0 |  |  |
| 3 | 2 | 3-0 |  |  |
| 3.5 | 3 | 2-0 |  |  |
| 4 | 3.5 | 0 |  |  |
| 5 | 4 | 1 |  |  |
| 6 | 5 | 2 |  |  |

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g. by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117 and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle siliconization process. Safeguards employed in an attempt to prevent the introduction of such foreign materials, e.g., water blocking during needle silconization, are inconvenient, adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

With regard to conventional detachable needles, a further disadvantage is that such needles heretofore have been attached by swaging or crimping. It is difficult to sufficiently control the swaging process in day to day manufacture so as to consistently obtain suture-needle devices which consistently detach under the same force with minimal variation in detachment force. Indeed, conventional swaged detachable needles have been observed to fail prematurely under minimal force, e.g. in removing the suture from the package, or to fail to yield under considerable force. Such events can result in unnecessary waste, lost time and, at worst, unavailability of a suture-needle to the surgeon when needed.

Commonly assigned, copending U.S. patent application Ser. No. 413,240, filed Sep. 27, 1989, describes a combined surgical needle-suture device and surgical needle-suture attachment method which overcomes the aforementioned drawbacks of the previously known needle-suture combinations and needle-suture attachment methods. In accordance with said application, a combined needle-suture device is provided in which a surgical needle having a shank of reduced cross-section is attached to a suture through a shrinkable tubing, or micro-ferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

SUMMARY OF THE INVENTION

It has now been found that relationships exist among the area, length and diameter of the tubing and the area, length and diameter of the shank of the needle and suture required to predictably and reliably achieve standard (i.e., ordinarily non-detachable) or selectively reversible (i.e., detachable) attachment of the needle and suture in the combined surgical needle-suture devices of aforementioned U.S. patent application Ser. No. 413,240.

In accordance With the present invention, there is provided a combined surgical needle-suture device which comprises:
 a) a needle having a shank of reduced cross-section;
 b) a suture; and,
 c) a shrinkable tubing around said needle shank and a portion of said suture, the ratio of the axial length of the tubing to the effective axial length of the needle shank being at least about 4:1 when the needle is intended to be non-detachable from the suture and no more than about 3.5:1 when the needle is intended to be detachable from the suture.

Further in accordance with this invention, there is provided a method for attaching a surgical needle to a suture to provide a combined surgical needle-suture device which comprises:
 a) providing a needle having a shank end of reduced cross-section;
 b) placing a shrinkable tubing around the reduced diameter shank and the suture, the ratio of the axial length of the tubing to the effective axial length of the needle shank being at least about 4:1 when the needle is intended to be non-detachable from the suture and no more than about 3.5:1 when the needle is intended to be detachable from the suture; and,
 c) applying energy to the shrinkable tubing to bring the tubing into engagement with the needle shank and suture.

It will be noted that for an entire line of surgical needles differing in length, diameter and configuration, attachment of the needles to their sutures in accordance with this invention can be accomplished with as few as two different axial lengths of tubing, the tubing of greater axial length being used for suture-needle devices of the non-detachable variety and the tubing of shorter axial length being used for suture-needle devices of the detachable variety. The use of such tubings makes it possible to minimize the number of different tubings which must be manufactured and inventoried to accommodate the needle-to-suture attachment needs of a comprehensive line of combined surgical needle-suture devices.

In a particularly preferred embodiment of the invention, it has been found that a detachable suture-needle combination can be provided which exhibits more consistent detachment (pull-out) force than known types of detachable needle-suture combinations of comparable size. More specifically, it has been found that a removal interface characterized by optimized suture tip surface characteristics in combination with optimized shrinkable tubing suture contact area results in a detachable suture-needle combination with a more consistent detachment force than the known types of standard detachable suture-needle combinations.

As used herein, the expression "standard needle-suture" refers to permanently attached needle-suture combinations in which the force required to separate the needle from the suture is within the range of pull-out force set forth in the *United States Pharmacopeia* for permanently attached needle-suture combinations.

As used herein, the expression "standard detachable needle-suture" refers to a detachable needle-suture combination in which the force to separate the needle from the suture is within the range of pull-out forces set forth in the *United States Pharmacopeia* for removable needle-suture combinations, and includes detachable or removable needle-suture combinations commercially available from Ethicon, Inc. (Johnson & Johnson) and Davis & Geck (American Cyanamid Co.)

BRIEF DESCRIPTION OF THE DRAWINGS

The present invention will become more apparent from the following detailed description taken in conjunction with the accompanying drawings in which.

DETAILED DESCRIPTION OF THE PREFERRED EMBODIMENTS

The present invention relates to a combined surgical needle-suture device and surgical needle-suture attachment method. The invention has application to any suture material whether absorbable or non-absorbable, natural or synthetic, braided or monofilament, and to any needle material and configuration whether straight or curved. The invention may be used to effect standard or detachable needle attachment as described in more detail below.

In the description of the invention herein and in the claims, the expression "effective axial length of the needle shank" shall be understood to include only so much of the length of the needle shank which is actually in contact with the interior wall of the tubing and excludes any portion of the length of the needle shank, for example, the rounded sections defined upon the butt end of the needle shank as disclosed in copending U.S. patent application Ser. No. 532,928, filed Jun. 4, 1990, which do not make contact with the interior wall of the tubing when the needle and its attached suture are aligned along a common axis.

The expression "effective axial length of the suture tip" shall be understood as identifying only that portion of the length of the suture tip which is actually in contact with the interior wall of the tubing and as excluding any portion of the length of the suture which does not contact the interior wall of the tubing when the tubing and its attached suture are aligned along a common axis.

Figure 1:
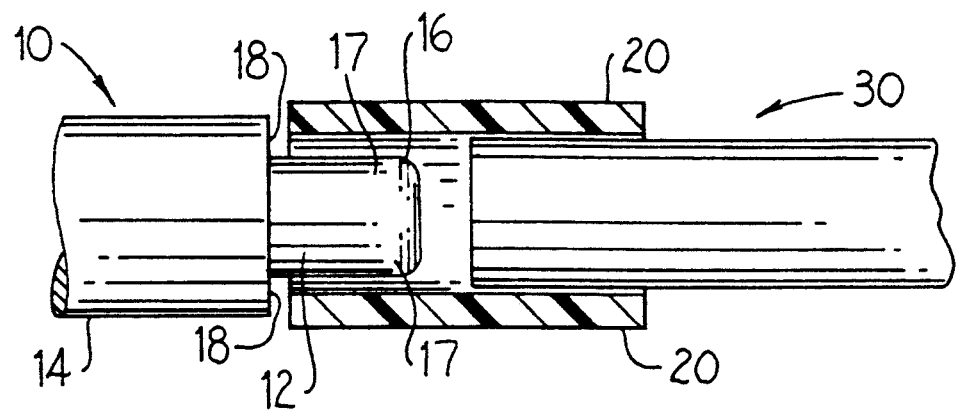
FIG. 1 is a side cross-sectional view of a needle and a suture with a tubing positioned therearound (prior to engagement of the tubing with the needle and suture)
Figure 2:
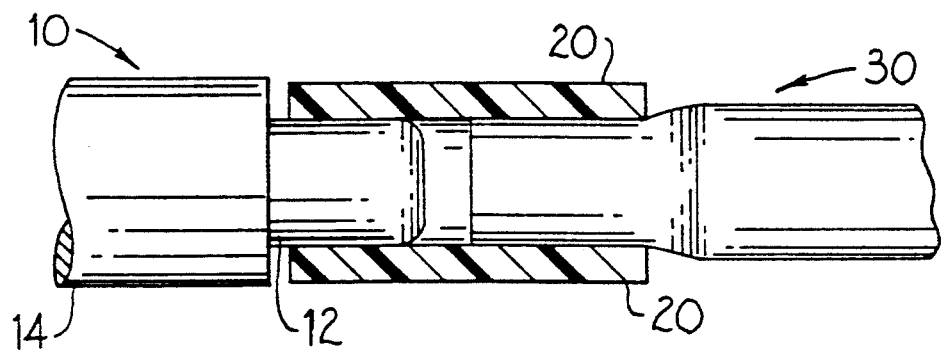
FIG. 2 is a side cross-sectional view of the tubing of FIG. 1 in engagement with the needle and suture; and, FIG. 3 is a side view of a combined surgical needle-suture device in accordance with the present invention.
Figure 3:
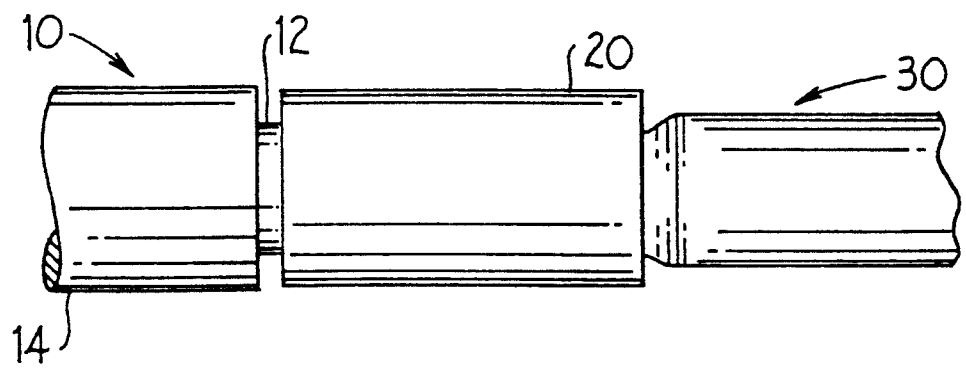
Figure 4:
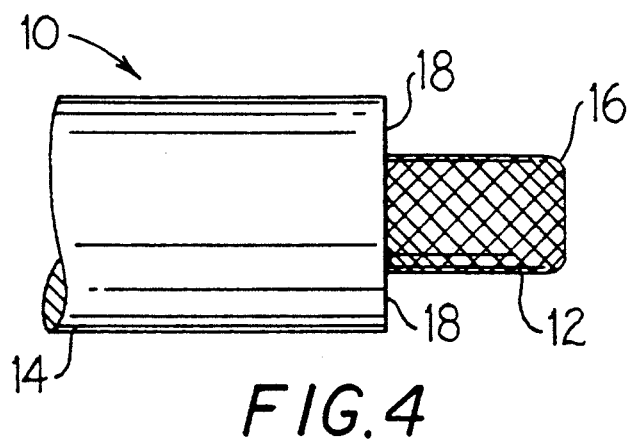
FIG. 4 is a side view of an alternative embodiment of the present invention in which the needle shank is scored.
Figure 5:
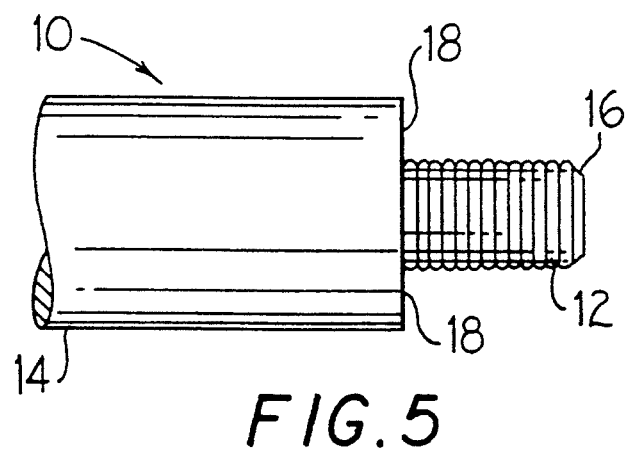
FIG. 5 is a side view of an alternative embodiment of the present invention in which the needle shank is ribbed.
Figure 6:
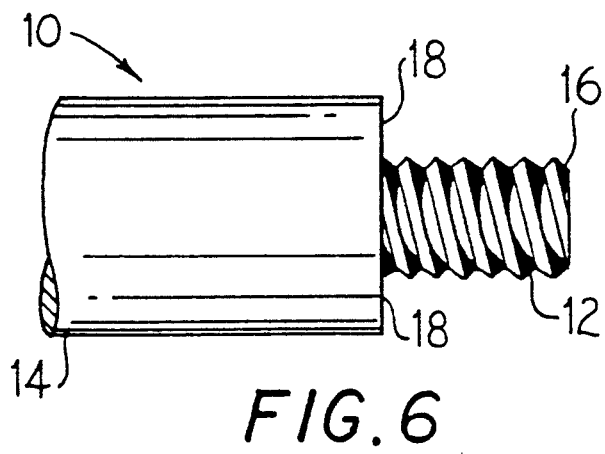
FIG. 6 is a side view of an alternative embodiment of the present invention in which the needle shank is threaded.
Figure 7:
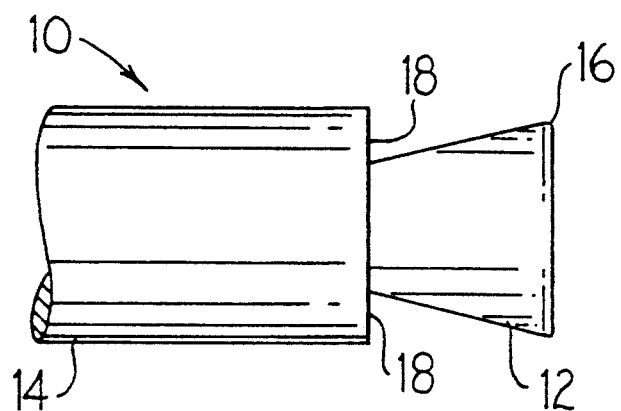
FIG. 7 is a side view of an alternative embodiment of the present invention in which the needle shank is tapered to expand in a direction away from a remainder of the needle; and, FIG. 8 is a side view of an alternative embodiment of the present invention in which the needle shank is tapered to expand in a direction towards the remainder of the needle.
Figure 8:
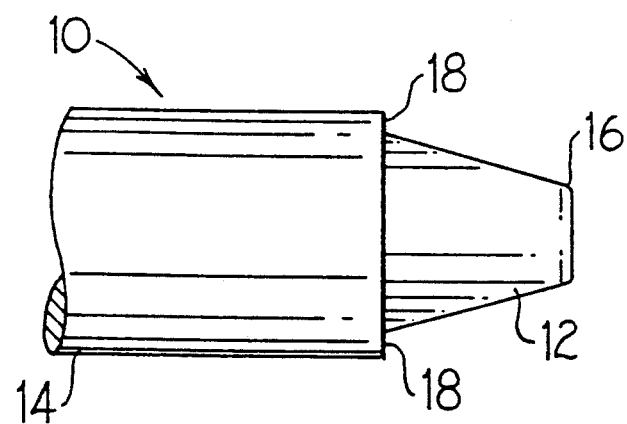

Referring to FIGS. 1-3, needle 10 has a reduced cross-sectional diameter at its shank 12 relative to the remainder of the needle 14. The diameter of needle shank 12 may be reduced by any conventional means, e.g., machining on a lathe. Typically, shank 12 has a diameter from 10 to 65% smaller than the remainder of needle 14, and preferably from 25 to 50% smaller. It is also possible to provide shank 12 with a texturized surface to facilitate gripping by shrinkable tubing 20. For example, shank 12 may be scored, (FIG. 4) ribbed (FIG. 5) or threaded (FIG. 6), in whole or in part. It may also be desirable to taper shank 12 such that its butt, or distal end 16 is of greater cross-sectional diameter than the cross-sectional diameter of shank 12 in the region of shoulder 18 (FIG. 7), or vice versa (FIG. 8).

Suture 30 is also positioned within shrinkable tubing, or micro-ferrule, 30. When, as shown in FIGS. 1-3, a gap exists between end 21 of tubing 20 and shoulder 18 of the needle, i.e., when tubing 20 extends for less than the full length of needle shank 12, the effective axial length of shank 12 will correspond only to that length of the shank which is actually in contact with the interior surface of the tubing. However, when the end 21 of tubing 20 abuts shoulder 18 of the needle (not shown), the effective axial length of shank 12 will be equivalent to its entire length.

When suture-needle device 10 is to be of the non-detachable variety, the ratio of the axial length of tubing 20 to the effective axial length of needle shank 12 must be at least about 4:1 and is preferably at least about 4.5:1. For practical reasons, it is preferable that this ratio not exceed about 12:1 and better yet, that it not exceed about 9.5:1. For the non-detachable variety of surgical needle-suture attachment, the material of construction of tubing 20 should be such that the tubing will withstand at least the USP minimum pull-out force for the appropriate suture size. If necessary or desirable, tubing 20 can be provided with a reinforcement, e.g., of carbon fibers, glass fibers, etc., to increase its tensile strength and thus improve the ability of the tubing to withstand the stress of a relatively high pull-out force.

When suture-needle device 10 is to be of the detachable variety, the ratio of the axial length of tubing 20 to the effective axial length of needle shank 12 must not exceed about 3.5:1, and preferably should not exceed about 3.2:1. Again, for practical considerations, it is preferable that this ratio be not less than about 1.2:1 and still more preferable that it be not less than about 1.4:1.

In Tables I and II below, specific ratios of the axial length of the tubing (ALT) to the effective axial length of the shank (EALS) are given for a variety of non-detachable and detachable combined surgical needle-suture devices manufactured from different types of sutures and needles. In these tables, the designations of the suture type have the following meanings:

| | |
|---|---|
| BRS - Braided Silk | BRD - Braided Dacron |
| BSA - Braided Synthetic Absorbable | BRN - Braided Nylon |
| PPM - Polypropylene Monofilament | SGC - Chromic Gut |

TABLE I

NON-DETACHABLE NEEDLE-SUTURE COMBINATIONS

| Suture Type | Suture Size | Needle Diameter/Inch | Shank Diameter/Inch | EALS/Inch | ALT/Inch | Ratio of ALT to EALS |
|---|---|---|---|---|---|---|
| BSA | 3/0 | .024 | .010 | .055 | .3–.5 | 5.5:1–9.1:1 |
| BRD | 3/0 | .024 | .010 | .055 | .3–.5 | 5.5:1–9.1:1 |
| BRS | 3/0 | .024 | .010 | .055 | .3–.5 | 5.5:1–9.1:1 |
| BRN | 3/0 | .024 | .010 | .055 | .3–.5 | 5.5:1–9.1:1 |
| BRN | 3/0 | .032 | .010 | .055 | .3–.5 | 5.5:1–9.1:1 |
| BRS | 4/0 | .032 | .010 | .055 | .3–.5 | 5.5:1–9.1:1 |
| BRS | 3/0 | .032 | .010 | .055 | .3–.5 | 5.5:1–9.1:1 |
| BRN | 4/0 | .032 | .010 | .055 | .3–.5 | 5.5:1–9.1:1 |
| BSA | 2/0 | .026 | .016 | .065 | .3–.5 | 4.6:1–7.7:1 |
| BRD | 2/0 | .026 | .016 | .065 | .3–.5 | 4.6:1–7.7:1 |
| BRS | 2/0 | .026 | .016 | .065 | .3–.5 | 4.6:1–7.7:1 |
| BRN | 2/0 | .026 | .016 | .065 | .3–.5 | 4.6:1–7.7:1 |
| SGC | 0 | .044 | .016 | .065 | .3–.5 | 4.6:1–7.7:1 |
| BSA | 0 | .044 | .016 | .065 | .3–.5 | 4.6:1–7.7:1 |
| SGC | 1 | .044 | .020 | .070 | .3–.5 | 4.3:1–7.1:1 |
| BSA | 1 | .044 | .020 | .070 | .3–.5 | 4.3:1–7.1:1 |
| BRD | 1 | .050 | .020 | .070 | .3–.5 | 4.3:1–7.1:1 |
| BRN | 1 | .050 | .020 | .070 | .3–.5 | 4.3:1–7.1:1 |
| BSA | 1 | .050 | .020 | .070 | .3–.5 | 4.3:1–7.1:1 |
| BRN | 1 | .039 | .020 | .070 | .3–.5 | 4.3:1–7.1:1 |
| SGC | 1 | .039 | .020 | .070 | .3–.5 | 4.3:1–7.1:1 |
| BRS | 3/0 | .039 | .010 | .055 | .3–.5 | 5.5:1–9.1:1 |
| BSA | 3/0 | .039 | .010 | .055 | .3–.5 | 5.5:1–9.1:1 |
| PPM | 2/0 | .039 | .016 | .065 | .3–.5 | 4.6:1–7.7:1 |
| BRS | 0 | .039 | .016 | .065 | .3–.5 | 4.6:1–7.7:1 |
| BRD | 2/0 | .039 | .016 | .065 | .3–.5 | 4.6:1–7.7:1 |
| PPM | 0 | .039 | .016 | .065 | .3–.5 | 4.6:1–7.7:1 |
| BRN | 2/0 | .039 | .016 | .065 | .3–.5 | 4.6:1–7.7:1 |
| BRD | 0 | .039 | .016 | .065 | .3–.5 | 4.6:1–7.7:1 |
| BSA | 2/0 | .039 | .016 | .065 | .3–.5 | 4.6:1–7.7:1 |
| SGC | 0 | .039 | .016 | .065 | .3–.5 | 4.6:1–7.7:1 |
| BRN | 0 | .039 | .016 | .065 | .3–.5 | 4.6:1–7.7:1 |
| BSA | 0 | .039 | .016 | .065 | .3–.5 | 4.6:1–7.7:1 |
| BRS | 2/0 | .039 | .016 | .065 | .3–.5 | 4.6:1–7.7:1 |
| BSA | 0 | .050 | .016 | .065 | .3–.5 | 4.6:1–7.7:1 |
| BRD | 0 | .050 | .016 | .065 | .3–.5 | 4.6:1–7.7:1 |
| BRN | 0 | .050 | .016 | .065 | .3–.5 | 4.6:1–7.7:1 |
| PPM | 0 | .050 | .016 | .065 | .3–.5 | 4.6:1–7.7:1 |
| PPM | 0 | .039 | .016 | .065 | .3–.5 | 4.6:1–7.7:1 |
| BRD | 0 | .039 | .016 | .065 | .3–.5 | 4.6:1–7.7:1 |
| BRN | 0 | .039 | .016 | .065 | .3–.5 | 4.6:1–7.7:1 |
| BSA | 2/0 | .039 | .016 | .065 | .3–.5 | 4.6:1–7.7:1 |
| BSA | 0 | .039 | .016 | .065 | .3–.5 | 4.6:1–7.7:1 |
| PPM | 2/0 | .039 | .016 | .065 | .3–.5 | 4.6:1–7.7:1 |
| BRD | 2/0 | .039 | .016 | .065 | .3–.5 | 4.6:1–7.7:1 |
| BRN | 2/0 | .039 | .016 | .065 | .3–.5 | 4.6:1–7.7:1 |
| BRS | 2/0 | .039 | .016 | .065 | .3–.5 | 4.6:1–7.7:1 |
| PPM | 0 | .044 | .016 | .065 | .3–.5 | 4.6:1–7.7:1 |
| PPM | 2/0 | .044 | .016 | .065 | .3–.5 | 4.6:1–7.7:1 |
| BRN | 4/0 | .020 | .010 | .055 | .3–.5 | 5.5:1–9.1:1 |
| BSA | 4/0 | .020 | .010 | .055 | .3–.5 | 5.5:1–9.1:1 |
| BRS | 4/0 | .020 | .010 | .055 | .3–.5 | 5.5:1–9.1:1 |
| BRS | 3/0 | .020 | .010 | .055 | .3–.5 | 5.5:1–9.1:1 |
| BRS | 2/0 | .020 | .010 | .055 | .3–.5 | 5.5:1–9.1:1 |
| BSA | 2/0 | .050 | .016 | .070 | .3–.5 | 4.3:1–7.1:1 |
| BSA | 0 | .050 | .016 | .070 | .3–.5 | 4.3:1–7.1:1 |
| SGC | 2/0 | .050 | .016 | .070 | .3–.5 | 4.3:1–7.1:1 |
| SGC | 0 | .050 | .016 | .070 | .3–.5 | 4.3:1–7.1:1 |
| BRN | 3/0 | .022 | .010 | .055 | .3–.5 | 5.5:1–9.1:1 |
| BRS | 3/0 | .022 | .010 | .055 | .3–.5 | 5.5:1–9.1:1 |
| BSA | 3/0 | .022 | .010 | .055 | .3–.5 | 5.5:1–9.1:1 |
| BRD | 0 | .050 | .016 | .065 | .3–.5 | 4.6:1–7.7:1 |
| BRD | 2/0 | .050 | .016 | .065 | .3–.5 | 4.6:1–7.7:1 |
| BRD | 0 | .050 | .016 | .065 | .3–.5 | 4.6:1–7.7:1 |
| BRS | 0 | .050 | .016 | .065 | .3–.5 | 4.6:1–7.7:1 |
| BRN | 0 | .050 | .016 | .065 | .3–.5 | 4.6:1–7.7:1 |
| PPM | 0 | .050 | .016 | .065 | .3–.5 | 4.6:1–7.7:1 |
| BRS | 2/0 | .050 | .016 | .065 | .3–.5 | 4.6:1–7.7:1 |
| BRN | 2/0 | .050 | .016 | .065 | .3–.5 | 4.6:1–7.7:1 |
| BRN | 3/0 | .039 | .010 | .055 | .3–.5 | 5.5:1–9.1:1 |
| SGC | 0 | .050 | .016 | .065 | .3–.5 | 4.6:1–7.7:1 |
| BRS | 0 | .060 | .016 | .065 | .3–.5 | 4.6:1–7.7:1 |
| PPM | 2/0 | .050 | .016 | .065 | .3–.5 | 4.6:1–7.7:1 |
| BRN | 0 | .050 | .016 | .065 | .3–.5 | 4.6:1–7.7:1 |
| BRN | 2/0 | .050 | .016 | .065 | .3–.5 | 4.6:1–7.7:1 |
| BRD | 2/0 | .050 | .016 | .065 | .3–.5 | 4.6:1–7.7:1 |
| PPM | 0 | .050 | .016 | .065 | .3–.5 | 4.6:1–7.7:1 |

TABLE I-continued

NON-DETACHABLE NEEDLE-SUTURE COMBINATIONS

| Suture Type | Suture Size | Needle Diameter/ Inch | Shank Diameter/ Inch | EALS/ Inch | ALT/ Inch | Ratio of ALT to EALS |
|---|---|---|---|---|---|---|
| BRN | 5/0 | .020 | .010 | .055 | .3–.5 | 5.5:1–9.1:1 |
| BSA | 5/0 | .020 | .010 | .055 | .3–.5 | 5.5:1–9.1:1 |
| BRS | 5/0 | .020 | .010 | .055 | .3–.5 | 5.5:1–9.1:1 |
| BRS | 5/0 | .020 | .010 | .055 | .3–.5 | 5.5:1–9.1:1 |

TABLE II

DETACHABLE NEEDLE-SUTURE COMBINATIONS

| Suture Type | Suture Size | Needle Diameter/ Inch | Shank Diameter/ Inch | EALS/ Inch | ALT/ Inch | Ratio of ALT to EALS |
|---|---|---|---|---|---|---|
| BSA | 3/0 | .024 | .010 | .055 | .095–.175 | 1.7:1–3.2:1 |
| BRD | 3/0 | .024 | .010 | .055 | .095–.175 | 1.7:1–3.2:1 |
| BRS | 3/0 | .024 | .010 | .055 | .095–.175 | 1.7:1–3.2:1 |
| BRN | 3/0 | .024 | .010 | .055 | .095–.175 | 1.7:1–3.2:1 |
| BRN | 3/0 | .032 | .010 | .055 | .095–.175 | 1.7:1–3.2:1 |
| BRS | 4/0 | .032 | .010 | .055 | .095–.175 | 1.7:1–3.2:1 |
| BRS | 3/0 | .032 | .010 | .055 | .095–.175 | 1.7:1–3.2:1 |
| BRN | 4/0 | .032 | .010 | .055 | .095–.175 | 1.7:1–3.2:1 |
| BSA | 2/0 | .026 | .016 | .065 | .095–.175 | 1.5:1–2.7:1 |
| BRD | 2/0 | .026 | .016 | .065 | .095–.175 | 1.5:1–2.7:1 |
| BRS | 2/0 | .026 | .016 | .065 | .095–.175 | 1.5:1–2.7:1 |
| BRN | 2/0 | .026 | .016 | .065 | .095–.175 | 1.5:1–2.7:1 |
| SGC | 0 | .044 | .016 | .065 | .095–.175 | 1.5:1–2.7:1 |
| BSA | 0 | .044 | .020 | .065 | .095–.175 | 1.5:1–2.7:1 |
| SGC | 1 | .044 | .020 | .070 | .095–.175 | 1.4:1–2.5:1 |
| BSA | 1 | .044 | .020 | .070 | .095–.175 | 1.4:1–2.5:1 |
| BRD | 1 | .050 | .020 | .070 | .095–.175 | 1.4:1–2.5:1 |
| BRN | 1 | .050 | .020 | .070 | .095–.175 | 1.4:1–2.5:1 |
| BSA | 1 | .050 | .020 | .070 | .095–.175 | 1.4:1–2.5:1 |
| BSA | 1 | .044 | .020 | .070 | .095–.175 | 1.4:1–2.5:1 |
| BRN | 1 | .039 | .020 | .070 | .095–.175 | 1.4:1–2.5:1 |
| SGC | 1 | .039 | .020 | .070 | .095–.175 | 1.4:1–2.5:1 |
| BRS | 3/0 | .039 | .010 | .055 | .095–.175 | 1.7:1–3.2:1 |
| BSA | 3/0 | .039 | .010 | .055 | .095–.175 | 1.7:1–3.2:1 |
| PPM | 2/0 | .039 | .016 | .065 | .095–.175 | 1.5:1–2.7:1 |
| BRS | 0 | .039 | .016 | .065 | .095–.175 | 1.5:1–2.7:1 |
| BRD | 2/0 | .039 | .016 | .065 | .095–.175 | 1.5:1–2.7:1 |
| PPM | 0 | .039 | .016 | .065 | .095–.175 | 1.5:1–2.7:1 |
| BRN | 2/0 | .039 | .016 | .065 | .095–.175 | 1.5:1–2.7:1 |
| BRD | 0 | .039 | .016 | .065 | .095–.175 | 1.5:1–2.7:1 |
| BSA | 2/0 | .039 | .016 | .065 | .095–.175 | 1.5:1–2.7:1 |
| SGC | 0 | .039 | .016 | .065 | .095–.175 | 1.5:1–2.7:1 |
| BRN | 0 | .039 | .016 | .065 | .095–.175 | 1.5:1–2.7:1 |
| BSA | 0 | .039 | .020 | .065 | .095–.175 | 1.5:1–2.7:1 |
| BRS | 2/0 | .039 | .016 | .065 | .095–.175 | 1.5:1–2.7:1 |
| BSA | 0 | .050 | .020 | .065 | .095–.175 | 1.5:1–2.7:1 |
| BRD | 0 | .050 | .016 | .065 | .095–.175 | 1.5:1–2.7:1 |
| BRN | 0 | .050 | .016 | .065 | .095–.175 | 1.5:1–2.7:1 |
| PPM | 0 | .050 | .016 | .065 | .095–.175 | 1.5:1–2.7:1 |
| PPM | 0 | .039 | .016 | .065 | .095–.175 | 1.5:1–2.7:1 |
| BRD | 0 | .039 | .016 | .065 | .095–.175 | 1.5:1–2.7:1 |
| BRN | 0 | .039 | .016 | .065 | .095–.175 | 1.5:1–2.7:1 |
| BSA | 2/0 | .039 | .016 | .065 | .095–.175 | 1.5:1–2.7:1 |
| BSA | 0 | .039 | .020 | .065 | .095–.175 | 1.5:1–2.7:1 |
| PPM | 2/0 | .039 | .016 | .065 | .095–.175 | 1.5:1–2.7:1 |
| BRD | 2/0 | .039 | .016 | .065 | .095–.175 | 1.5:1–2.7:1 |
| BRN | 2/0 | .039 | .016 | .065 | .095–.175 | 1.5:1–2.7:1 |
| BRS | 2/0 | .039 | .016 | .065 | .095–.175 | 1.5:1–2.7:1 |
| PPM | 0 | .044 | .016 | .065 | .095–.175 | 1.5:1–2.7:1 |
| PPM | 2/0 | .044 | .016 | .065 | .095–.175 | 1.5:1–2.7:1 |
| BRN | 4/0 | .020 | .010 | .055 | .095–.175 | 1.7:1–3.2:1 |
| BSA | 4/0 | .020 | .010 | .055 | .095–.175 | 1.7:1–3.2:1 |
| BRS | 4/0 | .020 | .010 | .055 | .095–.175 | 1.7:1–3.2:1 |
| BRS | 3/0 | .020 | .010 | .055 | .095–.175 | 1.7:1–3.2:1 |
| BRS | 2/0 | .020 | .010 | .055 | .095–.175 | 1.7:1–3.2:1 |
| BSA | 2/0 | .050 | .016 | .070 | .095–.175 | 1.4:1–2.5:1 |
| BSA | 0 | .050 | .020 | .070 | .095–.175 | 1.4:1–2.5:1 |
| SGC | 2/0 | .050 | .016 | .070 | .095–.175 | 1.4:1–2.5:1 |
| SGC | 0 | .050 | .016 | .070 | .095–.175 | 1.4:1–2.5:1 |
| BRN | 3/0 | .022 | .010 | .055 | .095–.175 | 1.7:1–3.2:1 |
| BRS | 3/0 | .022 | .010 | .055 | .095–.175 | 1.7:1–3.2:1 |
| BSA | 3/0 | .022 | .010 | .055 | .095–.175 | 1.7:1–3.2:1 |
| BRD | 0 | .050 | .016 | .065 | .095–.175 | 1.5:1–2.7:1 |
| BRD | 2/0 | .050 | .016 | .065 | .095–.175 | 1.5:1–2.7:1 |
| BRD | 0 | .050 | .016 | .065 | .095–.175 | 1.5:1–2.7:1 |
| BRS | 0 | .050 | .016 | .065 | .095–.175 | 1.5:1–2.7:1 |
| BRN | 0 | .050 | .016 | .065 | .095–.175 | 1.5:1–2.7:1 |
| PPM | 0 | .050 | .016 | .065 | .095–.175 | 1.5:1–2.7:1 |
| BRS | 2/0 | .050 | .016 | .065 | .095–.175 | 1.5:1–2.7:1 |
| BRN | 2/0 | .050 | .016 | .065 | .095–.175 | 1.5:1–2.7:1 |
| BRN | 3/0 | .039 | .010 | .055 | .095–.175 | 1.7:1–3.2:1 |
| SGC | 0 | .050 | .016 | .065 | .095–.175 | 1.5:1–2.7:1 |
| BRS | 0 | .060 | .016 | .065 | .095–.175 | 1.5:1–2.7:1 |
| PPM | 2/0 | .050 | .016 | .065 | .095–.175 | 1.5:1–2.7:1 |
| BRN | 0 | .050 | .016 | .065 | .095–.175 | 1.5:1–2.7:1 |
| BRN | 2/0 | .050 | .016 | .065 | .095–.175 | 1.5:1–2.7:1 |
| BRD | 2/0 | .050 | .016 | .065 | .095–.175 | 1.5:1–2.7:1 |
| PPM | 0 | .050 | .016 | .065 | .095–.175 | 1.5:1–2.7:1 |
| BRN | 5/0 | .020 | .010 | .055 | .095–.175 | 1.7:1–3.2:1 |
| BSA | 5/0 | .020 | .010 | .055 | .095–.175 | 1.7:1–3.2:1 |
| BRS | 5/0 | .020 | .010 | .055 | .095–.175 | 1.7:1–3.2:1 |
| BRS | 5/0 | .020 | .010 | .055 | .095–.175 | 1.7:1–3.2:1 |

A gap may exist between shank 12 and suture 30 (as shown in FIGS. 1 and 2) or shank 12 may abut against suture 30. As shown in FIG. 1, suture 30 may initially be of uniform cross-section throughout its length. Alternatively, the tip region of suture 30, i.e., the region inserted into tubing 20, may be of reduced cross-section relative to the remainder of suture 30, e.g., by tipping the suture tip with an adhesive or resinous tipping agent while suture 30 is under tension. (See, e.g., Canadian Patent No. 1,009,532 to Messores.) Reducing the diameter of the suture tip as by resin tipping may be desirable to prevent brooming of the suture, particularly for multifilament braided sutures, to rigidify the end of the suture to facilitate handling during attachment, and to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of the tip region of suture 30 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of the tip region of suture 30, thereby removing the importance or criticality of suture tipping.

After shrinkable tubing 20 is placed around shank 12 of needle 10 and the tip region of suture 30, energy is applied to tubing 20. In response to this energy, tubing 20 contracts or shrinks and engages shank 12 and suture 30. The overall length of tubing 20 may also be affected by the application of energy, e.g., the length of tubing 20 may reduce. Thus, the shrinking of tubing 20 brings the inner surface of tubing 20 into engagement with shank 12 and suture 30, thereby securing suture 30 to needle 10. Suitable energy sources include heat (convective or conductive), radiation, microwave energy, etc.

As shown in FIGS. 1 and 2, shrinkable tubing 20 is simultaneously placed around both suture 30 and shank 12 of needle 10 in one embodiment of the present invention. It is preferable, however, to sequentially secure tubing 20 to needle 10 and suture 30. Thus, in a preferred embodiment of the present invention, shrinkable tubing 20 is initially secured to shank 12 through the localized application of energy to tubing 20 in the region surrounding shank 12. After tubing 20 has been brought into engagement with shank 12, suture 30 is inserted into tubing 20 and additional energy is applied thereto. Sequential shrinkage of tubing 20 makes it possible to vary the amount of energy used in securing tubing 20 to shank 12 and suture 30, respectively, and to limit the exposure of suture 30 to energy during the attachment process. It may also be desirable to cool suture 30 in the region outside tubing 20 to prevent any undesirable degradation thereof, e.g., with a cold air curtain.

As shown in FIGS. 2 and 3, the shrinkage of tubing 20 typically compresses suture 30 to some extent. This is particularly true where the suture is a braided, multifilament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 may be manufactured from any material which shrinks, i.e., reduces in diameter, in response to the application of energy. Suitable materials for tubing 20 include shrinkable plastic materials such as polyvinylidene fluoride materials available from Raychem Corporation, Menlo Park, Calif., under the tradename Kynar. Shrinkable polyolefins are also suitable, particularly for surgical gut suture attachment since polyolefins are resistant to attack by the isopropyl alcohol storage fluid in which gut sutures are commonly packaged. As previously noted, the materials from which shrinkable tubing 20 is manufactured can be provided with fibrous reinforcements to increase their tensile strengths. Tubing 20 is typically extruded in such a manner that its inner diameter will be less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink or "recover" to its original extruded inner diameter in response to the application of a predetermined amount of energy.

The amount of energy applied to tubing 20 to effect the desired attachment, i.e., diameter reduction, depends upon the chemical characteristics of the tubing material, the relative dimensions of the tubing, the shank end of the needle and the suture, and the desired pull-out force for the needle-suture combination. For example, one polyvinylidene fluoride material available from Raychem Corporation (RT-850) shrinks at temperatures greater than 175° C., and is adapted to recover to about 50% of its radially expanded inner diameter. In such case, tubing 20 may be brought into engagement with shank 12 of needle 10 and suture 30, either simultaneously or sequentially, by heating tubing 20 to a temperature above 175° C. Tubing 20 may be heated through contact with a hot gas stream or with heated dies, or by other heating means. Typically, the outer diameters of shank 12 and suture 30 (in the region inserted into tubing 20) are greater than the fully recovered diameter of tubing 20, e.g., greater than 50% of the initial inner diameter of tubing 20 for the RT-850 material, such that tubing 20 engages shank 12 and suture 30. This engagement provides the needle-suture combination of the present invention.

As noted above, the attachment method of the present invention may be easily used to effect both standard needle attachment and detachable needle attachment. Preferably, the pull-out force of a given needle-suture combination is controlled through control of the energy source and the surface contact area of the removal interface between the tubing on the one hand and needle and/or suture tip on the other. Thus, using the identical inventories of needles, sutures and tubings, it is possible to produce either standard or detachable needle products through simple energy variations. In the case of detachable needle attachment, it is preferred that the attachment conditions be controlled such that the tubing remains secured to the needle once the suture is detached.

The needle-suture attachment method of the present invention has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method of the present invention is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations.

Needle-suture combinations produced according to the present invention are atraumatic and advantageously exhibit flexibility in the attachment region. Both standard needle attachment and detachable needle attachment products may be produced with great processing ease.

The foregoing combinations provide reliable permanent and detachable needle-suture combinations which satisfy USP requirements. In addition, the present invention now makes it possible to provide a detachable needle-suture combination having a detachment force which is more consistent than the detachment force of standard detachable needle-suture combinations. To accomplish this highly desirable results, it has been found that the parameters set out in Table III below are most preferred. In Table III, the optimized contact areas between the shrinkable tubing and the needle and suture are set forth as a function of tube, needle shank and suture tip diameters and length. In addition, specific ratios of the approximate axial length of the tubing (ALT) to the approximate effective axial length of the shank (EALS) and to the approximate effective axial length of the suture tip (EALT) are set forth.

The areas, lengths, diameters and ratios set forth in Tables I through III relate to tube lengths and ratios prior to shrinking of the tube. The optimized suture contact area has been estimated by calculating the approximate surface area of the suture tip placed within the tube prior to shrinking the tube. It will be understood that the actual contact surface area after shrinking the tube may differ from the pre-shrink calculated area, but the calculated area is believed to provide a reasonable indication of the attached structure. Furthermore, the axial length, and consequently the contact area, of the tube may alter somewhat, e.g. decrease, during shrinking, but it is desirable to minimize changes in the axial length of the tubing during shrinking and maximize recovery of the tube in the radial direction so as to provide a relatively constant tube length and contact area. Indeed, in the context of detachable needles having more consistent pull-out force it is important to provide a relatively constant contact area between the inner surface of the tubing and the surface to be released from the tubing upon application of a predetermined pull-out force. In addition, in the context of removable needles, it is desirable to have the tubing remain attached to the needle shank, with detachment occurring at the interface of the tubing with the suture tip. The parameters set forth in Table III provide a removable needle-suture combination wherein detachment occurs between the tubing and the suture under application of a consistently reliable pull-out force.

TABLE III

PREFERRED DETACHABLE NEEDLE-SUTURE COMBINATIONS

| Suture Type | Suture Size | Needle Diameter/ Inch | Shank Diameter/ Inch | EALS/ Inch | ALT/ Inch | Ratio of ALT to EALS | Ratio of ALT to EALT | Average Suture Tip Diam. (Inch) | Approximate Suture Tip/ Tube Contact Area (In$^2$) |
|---|---|---|---|---|---|---|---|---|---|
| BSA | 3/0 | .024 | .010 | .055 | .125 | 2.27 | 1.79 | .012 | .0026 |
| BRD | 3/0 | .024 | .010 | .055 | .125 | 2.27 | 1.79 | .010 | .0022 |
| BRS | 3/0 | .024 | .010 | .055 | .125 | 2.27 | 1.79 | .011 | .0024 |
| BRN | 3/0 | .024 | .010 | .055 | .125 | 2.27 | 1.79 | .010 | .0022 |
| BRN | 3/0 | .032 | .010 | .055 | .125 | 2.27 | 1.79 | .010 | .0022 |
| BRS | 4/0 | .032 | .010 | .055 | .125 | 2.27 | 1.79 | .009 | .0020 |
| BRS | 3/0 | .032 | .010 | .055 | .125 | 2.27 | 1.79 | .011 | .0024 |
| BRN | 4/0 | .032 | .010 | .055 | .125 | 2.27 | 1.79 | .008 | .0018 |
| BSA | 2/0 | .026 | .016 | .065 | .125 | 1.92 | 2.08 | .017 | .0032 |
| BRD | 2/0 | .026 | .016 | .065 | .125 | 1.92 | 2.08 | .013 | .0025 |
| BRS | 2/0 | .026 | .016 | .065 | .125 | 1.92 | 2.08 | .015 | .0028 |
| BRN | 2/0 | .026 | .016 | .065 | .125 | 1.92 | 2.08 | .014 | .0026 |
| SGC | 0 | .044 | .016 | .065 | .115 | 1.77 | 2.30 | .016 | .0025 |
| BSA | 0 | .044 | .016 | .065 | .115 | 1.77 | 2.30 | .019 | .0030 |
| SGC | 1 | .044 | .020 | .070 | .115 | 1.64 | 2.56 | .019 | .0027 |
| BSA | 1 | .044 | .020 | .070 | .115 | 1.64 | 2.56 | .023 | .0033 |
| BRD | 1 | .050 | .020 | .070 | .125 | 1.79 | 2.27 | .018 | .0031 |
| BRN | 1 | .050 | .020 | .070 | .125 | 1.64 | 2.56 | .020 | .0035 |
| BSA | 1 | .050 | .020 | .070 | .115 | 1.64 | 2.56 | .023 | .0033 |
| BRN | 1 | .039 | .020 | .070 | .125 | 1.79 | 2.27 | .020 | .0035 |
| SGC | 1 | .039 | .020 | .070 | .115 | 1.64 | 2.56 | .019 | .0027 |
| BRS | 3/0 | .039 | .010 | .055 | .125 | 2.27 | 1.79 | .015 | .0028 |
| BSA | 3/0 | .039 | .010 | .055 | .125 | 2.27 | 1.79 | .012 | .0023 |
| PPM | 2/0 | .039 | .016 | .065 | .125 | 1.92 | 2.08 | .013 | .0025 |
| BRS | 0 | .039 | .016 | .065 | .125 | 1.92 | 2.08 | .017 | .0032 |
| BRD | 2/0 | .039 | .016 | .065 | .125 | 1.92 | 2.08 | .013 | .0025 |
| PPM | 0 | .039 | .016 | .065 | .125 | 1.92 | 2.08 | .015 | .0028 |
| BRN | 2/0 | .039 | .016 | .065 | .125 | 1.92 | 2.08 | .014 | .0026 |
| BRD | 0 | .039 | .016 | .065 | .125 | 1.92 | 2.08 | .016 | .0030 |
| BSA | 2/0 | .039 | .016 | .065 | .125 | 1.92 | 2.08 | .017 | .0032 |
| SGC | 0 | .039 | .016 | .065 | .115 | 1.77 | 2.30 | .016 | .0025 |
| BRN | 0 | .039 | .016 | .065 | .125 | 1.92 | 2.08 | .017 | .0032 |
| BSA | 0 | .039 | .016 | .065 | .115 | 1.77 | 2.30 | .019 | .0030 |
| BRS | 2/0 | .039 | .016 | .065 | .125 | 1.92 | 2.08 | .015 | .0028 |
| BSA | 0 | .050 | .016 | .065 | .115 | 1.77 | 2.30 | .019 | .0030 |
| BRD | 0 | .050 | .016 | .065 | .125 | 1.92 | 2.08 | .016 | .0030 |
| BRN | 0 | .050 | .016 | .065 | .125 | 1.92 | 2.08 | .017 | .0032 |
| PPM | 0 | .050 | .016 | .065 | .125 | 1.92 | 2.08 | .015 | .0028 |
| PPM | 0 | .039 | .016 | .065 | .125 | 1.92 | 2.08 | .015 | .0028 |
| BRD | 0 | .039 | .016 | .065 | .125 | 1.92 | 2.08 | .016 | .0030 |
| BRN | 0 | .039 | .016 | .065 | .125 | 1.92 | 2.08 | .017 | .0032 |
| BSA | 2/0 | .039 | .016 | .065 | .125 | 1.92 | 2.08 | .017 | .0032 |
| BSA | 0 | .039 | .016 | .065 | .115 | 1.77 | 2.30 | .019 | .0030 |
| PPM | 2/0 | .039 | .016 | .065 | .125 | 1.92 | 2.08 | .013 | .0025 |
| BRD | 2/0 | .039 | .016 | .065 | .125 | 1.92 | 2.08 | .013 | .0025 |
| BRN | 2/0 | .039 | .016 | .065 | .125 | 1.92 | 2.08 | .014 | .0026 |
| BRS | 2/0 | .039 | .016 | .065 | .125 | 1.92 | 2.08 | .015 | .0028 |
| PPM | 0 | .044 | .016 | .065 | .125 | 1.92 | 2.08 | .015 | .0028 |
| PPM | 2/0 | .044 | .016 | .065 | .125 | 1.92 | 2.08 | .013 | .0025 |
| BRN | 4/0 | .020 | .010 | .055 | .125 | 2.27 | 1.79 | .008 | .0018 |
| BSA | 4/0 | .020 | .010 | .055 | .125 | 2.27 | 1.79 | .010 | .0022 |
| BRS | 4/0 | .020 | .010 | .055 | .125 | 2.27 | 1.79 | .009 | .0020 |
| BRS | 3/0 | .020 | .010 | .055 | .125 | 2.27 | 1.79 | .011 | .0024 |
| BRS | 2/0 | .020 | .010 | .055 | .125 | 2.27 | 1.79 | .015 | .0033 |

TABLE III-continued
PREFERRED DETACHABLE NEEDLE-SUTURE COMBINATIONS

| Suture Type | Suture Size | Needle Diameter/ Inch | Shank Diameter/ Inch | EALS/ Inch | ALT/ Inch | Ratio of ALT to EALS | Ratio of ALT to EALT | Average Suture Tip Diam. (Inch) | Approximate Suture Tip/ Tube Contact Area (In$^2$) |
|---|---|---|---|---|---|---|---|---|---|
| BSA | 2/0 | .050 | .016 | .070 | .125 | 1.79 | 2.27 | .017 | .0029 |
| BSA | 0 | .050 | .016 | .070 | .115 | 1.64 | 2.56 | .019 | .0027 |
| SGC | 2/0 | .050 | .016 | .070 | .115 | 1.64 | 2.56 | .014 | .0020 |
| SGC | 0 | .050 | .016 | .070 | .115 | 1.64 | 2.56 | .016 | .0023 |
| BRN | 3/0 | .022 | .010 | .055 | .125 | 2.27 | 1.79 | .010 | .0019 |
| BRS | 3/0 | .022 | .010 | .055 | .125 | 2.27 | 1.79 | .011 | .0024 |
| BSA | 3/0 | .022 | .010 | .055 | .125 | 2.27 | 1.79 | .012 | .0026 |
| BRD | 0 | .050 | .016 | .065 | .125 | 1.92 | 2.08 | .016 | .0030 |
| BRD | 2/0 | .050 | .016 | .065 | .125 | 1.92 | 2.08 | .013 | .0025 |
| BRD | 0 | .050 | .016 | .065 | .125 | 1.92 | 2.08 | .016 | .0030 |
| BRS | 0 | .050 | .016 | .065 | .115 | 1.77 | 2.30 | .017 | .0027 |
| BRN | 0 | .050 | .016 | .065 | .125 | 1.92 | 2.08 | .017 | .0032 |
| PPM | 0 | .050 | .016 | .065 | .125 | 1.92 | 2.08 | .015 | .0028 |
| BRS | 2/0 | .050 | .016 | .065 | .125 | 1.92 | 2.08 | .015 | .0028 |
| BRN | 2/0 | .050 | .016 | .065 | .125 | 1.92 | 2.08 | .014 | .0026 |
| BRN | 3/0 | .039 | .010 | .055 | .125 | 2.27 | 1.79 | .010 | .0022 |
| SGC | 0 | .050 | .016 | .065 | .115 | 1.77 | 2.30 | .016 | .0025 |
| BRS | 0 | .060 | .016 | .065 | .125 | 1.92 | 2.08 | .017 | .0032 |
| PPM | 2/0 | .050 | .016 | .065 | .125 | 1.92 | 2.08 | .013 | .0025 |
| BRN | 0 | .050 | .016 | .065 | .125 | 1.92 | 2.08 | .017 | .0032 |
| BRN | 2/0 | .050 | .016 | .065 | .125 | 1.92 | 2.08 | .014 | .0026 |
| BRD | 2/0 | .050 | .016 | .065 | .125 | 1.92 | 2.08 | .010 | .0019 |
| PPM | 0 | .050 | .016 | .065 | .125 | 1.92 | 2.08 | .015 | .0028 |
| BSA | 5/0 | .020 | .010 | .055 | .125 | 2.27 | 1.79 | .009 | .0020 |

In the preferred detachable needle-suture configurations of Table III, three different tubings were used whose additional dimensional characteristics are set forth in Table IV as follows:

TABLE IV
ADDITIONAL DIMENSIONAL CHARACTERISTICS OF THE TUBING EMPLOYED IN THE PREFERRED DETACHABLE NEEDLE-SUTURE COMBINATION OF TABLE III

| Tubing | Suture Size | Shank Diameter/ Inch | Tubing Dimensions | | |
|---|---|---|---|---|---|
| | | | Minimum Expanded Inner Diameter/ Inch | Maximum Recovered Inner Diameter/ Inch | Maximum Recovered Wall Thickness/ Inch |
| 1 | 3/0, 4/0 | .010 | .014 | .007 | .0055 |
| 2 | 0, 2/0 | .016 | .018 | .012 | .0065 |
| 3 | 1 | .020 | .025 | .016 | .009 |

The lengths of the tubings are preferably to within about ±0.015 inch, more preferably to within about ±0.010 inch and most preferably to within about ±0.005 inch. In order to accommodate small changes in braid diameter, it is contemplated that the tube could be as long as about 0.140 inch and possibly as long as about 0.155 to about 0.160 inch. Based on the pre-attachment length of the preferred tubing, the effective axial length of the needle shank and the average tip diameter of the various types and sizes of suture, it can be seen that the contact area between the effective axial length of the suture tip and the tubing will range from about 0.001 square inches to about 0.008 square inches, preferably from about 0.001 to about 0.006 square inches, and that the axial length of the contact area ranges from about 0.045 inches to about 0.105 inches.

Broad and preferred tube to suture contact areas for each size suture are summarized in Table V.

TABLE V
REMOVAL INTERFACE CONTACT AREA BY SUTURE SIZE

| Suture Size | Broad Suture Tip Diameter (In.) | Broad Tube Contact Length (In.) | Broad Contact Area (In$^2$) |
|---|---|---|---|
| (Part 1 - Broad) | | | |
| 1 | .016 to .024 | .045 to .105 | .0023 to .0079 |
| 0 | .014 to .020 | .045 to .105 | .0020 to .0066 |
| 2/0 | .012 to .017 | .045 to .105 | .0017 to .0053 |
| 3/0 | .008 to .013 | .045 to .105 | .0011 to .0043 |
| 4/0 | .006 to .010 | .045 to .105 | .0008 to .0033 |
| 5/0 | .004 to .009 | .045 to .105 | .0006 to .0030 |
| (Part 2 Preferred) | | | |
| 1 | .018 to .022 | .060 to .090 | .0034 to .0062 |
| 0 | .015 to .019 | .060 to .090 | .0028 to .0054 |
| 2/0 | .012 to .016 | .060 to .090 | .0023 to .0048 |
| 3/0 | .010 to .012 | .060 to .090 | .0019 to .0034 |
| 4/0 | .008 to .010 | .060 to .090 | .0015 to .0028 |
| 5/0 | .006 to .009 | .060 to .090 | .0011 to .0025 |

In order to further optimize the suture pull-out force, it is important to provide a consistently smooth surface to engage the shrinkable tubing at the detachment contact area. Thus, in the preferred embodiment wherein detachment occurs between the tubing and the suture tip, it is important to provide a smooth, consistent suture tip surface area. Monofilament sutures by their nature provide such a smooth consistent tip surface. Braided sutures, however, inherently possess a relatively rougher and less consistent surface which may vary slightly in diameter. For these and other reasons, a tipping composition is applied in order to optimize the surface of the tip regions of braided sutures. The preferred tipping agent is a cyanoacrylate resin applied using an ultrasonic spray apparatus as described in co-pending U.S. patent application Ser. No. 07/626,995, filed Dec. 13, 1990, the entire contents of which are incorporated by reference herein.

Due to variations in the receptivity of various suture materials to the cyanoacrylate tipping agent, it is further preferred that the cyanoacrylate tipping agent be applied by passing the suture region to be tipped through the ultrasonic spray produced by the foregoing apparatus. It has been found that in most cases, from one to five passes through the spray will result in the desired suture tip surface. Preferred numbers of passes through the apparatus for various types of materials are set out below in Table VI:

TABLE VI

PREFERRED NUMBER OF PASSES THROUGH ULTRASONIC SPRAYING APPARATUS FOR DIFFERENT TYPES OF SUTURES TO ACCOMPLISH OPTIMIZED CYANOACRYLATE TIPPING

| Suture Material | Number of Passes |
| --- | --- |
| Braided Dacron (DuPont) | 1–3 |
| Braided nylon | 2–5 |
| Braided silk | 1–2 |
| Braided synthetic absorbable resin | 2–4 |

The following examples demonstrate the improved consistency of pull-off forces for removable needle-suture combinations constructed in accordance with the invention, specifically those described in Table III above.

EXAMPLES 1–7 AND COMPARISON EXAMPLES 1–7

Monofilament polypropylene (dyed) braided synthetic absorbable and braided black nylon sutures of various sizes were attached to needles in accordance with the parameters set forth in Table III. In accordance with the preferred embodiment of the invention, the needle shank was grooved, or ribbed (approximately 4 evenly spaced grooves about 0.0005 inch deep). Twenty samples of each suture type and size were tested for pull-off force and the average pull-off force and standard deviation were determined. For comparison purposes, the same number of comparable standard detachable needle-suture combinations available from Ethicon Inc, (Johnson & Johnson) were tested to determine average pull-out force and standard deviation. The results of these tests are set forth in Table VII below.

TABLE VII

STANDARD DEVIATION IN MINIMUM PULL-OUT FORCES FOR VARIOUS DETACHABLE SUTURE-NEEDLE COMBINATIONS

| | Suture Size | Suture Material | Average Pull-out Force (kg) | Standard Deviation |
| --- | --- | --- | --- | --- |
| Example 1 | 0 | Braided synthetic absorbable | 0.465 | 0.146 |
| Comparison Example 1 | 0 | Braided synthetic absorbable | 0.616 | 0.192 |
| Example 2 | 4/0 | Braided synthetic absorbable | 0.268 | 0.052 |
| Comparison Example 2 | 4/0 | Braided synthetic absorbable | 0.323 | 0.093 |
| Example 3 | 0 | Monofilament polypropylene | 0.206 | 0.049 |
| Comparison Example 3 | 0 | Monofilament polypropylene | 0.574 | 0.148 |
| Example 4 | 2/0 | Monofilament polypropylene | 0.181 | 0.034 |
| Comparison Example 4 | 2/0 | Monofilament polypropylene | 0.503 | 0.147 |
| Example 5 | 2/0 | Braided black nylon | 0.213 | 0.042 |
| Comparison Example 5 | 2/0 | Braided black nylon | 0.429 | 0.169 |
| Example 6 | 3/0 | Braided black nylon | 0.180 | 0.032 |
| Comparison Example 6 | 3/0 | Braided black nylon | 0.419 | 0.115 |
| Example 7 | 0 | Braided black nylon | 0.292 | 0.114 |
| Comparison Example 7 | 0 | Braided black nylon | 0.820 | 0.253 |

The foregoing data demonstrate that in most cases, preferred needle-suture combinations of this invention provide a removable needle-suture having a lower standard deviation in removal force than the known standard detachable needle-suture combinations and significantly lower in many cases, e.g., from about 20% to about 70% lower standard deviation. More consistent pull-out force translates into perceptible improvement in the reliability of removable sutures in accordance with the invention. Because removable needles must meet individual minimum pull-out force requirements, reduced variation in pull-out force also makes it possible to provide removable needle-suture combinations having a lower average pull-out force than standard detachable needles while also ensuring that individual sutures will not fall below individual pull-out force requirements.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A combined surgical needle-suture device which comprises:
   (a) a needle having a shank of reduced cross-section;
   (b) a suture; and,
   (c) a shrinkable tubing around said needle shank and a portion of said suture, the ratio of the axial length of the tubing to the effective axial length of the needle shank being at least about 4:1 when the needle is intended to be non-detachable from the suture and no more than about 3.5:1 when the needle is intended to be detachable from the suture.

2. The combined surgical needle-suture device of claim 1 wherein the device is of the non-detachable type and said ratio is at least about 4.5:1.

3. The combined surgical needle-suture device of claim 1 wherein the device is of the non-detachable type and said ratio does not exceed about 12:1.

4. The combined surgical needle-suture device of claim 1 wherein the device is of the non-detachable type and said ratio does not exceed about 9.5:1.

5. The combined surgical needle-suture device of claim 1 wherein the device is of the detachable type and said ratio does not exceed about 3.2:1.

6. The combined surgical needle-suture device of claim 1 wherein the device is of the detachable type and said ratio is not less than about 1.2:1.

7. The combined surgical needle-suture device of claim 1 wherein the device is of the detachable type and said ratio is not less than about 1.4:1.

8. The combined surgical needle-suture device of claim 1 wherein the device is of the detachable type and said ratio is in the range of about 1.6 to 2.3.

9. The combined surgical needle-suture device of claim 1 wherein the device is of the detachable type and said shrinkable tubing has an axial length of about 0.125 inch.

10. The combined surgical needle-suture device of claim 1 wherein the device is of the detachable type and said shrinkable tubing has an axial length of about 0.115 inch.

11. The combined surgical needle-suture device of claim 1 wherein the ratio of the axial length of the tubing to the effective axial length of the suture tip is in the range of from about 1.8 to about 2.6.

12. The combined surgical needle-suture device of claim 1 wherein the axial length of the tubing is in the range of from about 0.115 to about 0.160 inches.

13. A plurality of combined surgical needle-suture devices, each such device comprising:
(a) a needle having a shank of reduced cross-section;
(b) a suture; and,
(c) a shrinkable tubing around said needle shank and a portion of said suture, a surface contact area defined between said shrinkable tubing and at least one of said needle shank and/or suture to provide a detachable needle-suture device, said surface contact area having an effective axial length in the range of from about 0.045 to about 0.105 inch; and, each said needle-suture combination meeting the pull-out force limits for removable needle attachment set forth in the United States Pharmacopeia and said plurality of needle-suture combinations exhibiting a standard deviation in average pull-out force of less than or equal to about 0.15.

14. A combined surgical needle-suture device which comprises:
(a) a needle having a shank of reduced cross-section;
(b) a suture; and
(c) a shrinkable tubing around said needle shank and a portion of said suture, a surface contact area defined between said shrinkable tubing and at least one of said needle shank and/or suture to provide a detachable needle-suture device, said surface contact area having an effective axial length in the range of from about 0.045 to about 0.105 inch, wherein the ratio of the axial length of the tubing to the effective axial length of the needle shank does not exceed about 3.5:1.

15. The combined surgical needle-suture device of claim 14 wherein said ratio is in the range of from about 1.6 to about 2.3.

16. A combined surgical needle-suture device which comprises:
(a) a needle having a shank of reduced cross-section;
(b) a suture; and,
(c) a shrinkable tubing having an axial length in the range of from about 0.115 to about 0.160 inches, the shrinkable tubing disposed around the needle shank and a portion of said suture to join the suture and needle defining a pull-out force for a detachable needle-suture combination.

17. A method for attaching a surgical needle to a suture comprising:
(a) providing a needle having a shank of reduced cross-section;
(b) placing a shrinkable tubing around the reduced diameter shank and the suture, the axial length of the tubing to the effective axial length of the needle shank being at least about 4:1 when the needle is intended to be non-detachable from the suture and no more than about 3.5:1 when the needle is intended to be detachable from the suture; and,
(c) applying energy to the shrinkable tubing to bring the tubing into engagement with the needle shank and suture.

18. The method of claim 17 wherein the device is of the non-detachable type and said ratio is at least 4.5:1.

19. The method of claim 17 wherein the device is of the non-detachable type and said ratio does not exceed about 12:1.

20. The method of claim 17 wherein the device is of the non-detachable type and said ratio does not exceed about 9.5:1.

21. The method of claim 17 wherein the device is of the detachable type and said ratio does not exceed about 3.2:1.

22. The method of claim 17 wherein the device is of the detachable type and said ratio is not less than about 1.2:1.

23. The method of claim 17 wherein the device is of the detachable type and said ratio is not less than about 1.4:1.

24. The method of claim 17 wherein the device is of the detachable type and said ratio is in the range of from about 1.6 to about 2.3.

25. The method of claim 17 wherein the device is of the detachable type and said tubing has an axial length in the range of from about 0.115 to about 0.160 inches.

26. A method for attaching a plurality of surgical needles to sutures to provide a plurality of detachable needle-suture devices comprising:
(a) providing a plurality of needles having a shank of reduced cross-section;
(b) placing a shrinkable tubing around each reduced needle shank and a suture;
(c) applying energy to the shrinkable tubing to bring the tubing into engagement with the needle shank and suture so as to define a surface contact area between each shrinkable tubing and the needle shank, the suture or the needle shank and the suture, the surface contact area having an effective axial length in the range of from about 0.045 to about 0.105 inches, and,
(d) controlling said energy application to provide a plurality of devices meeting the pull-out force limits for removable needle attachment set forth in the United states Pharmacopeia and exhibiting a standard deviation in average pull-out force of less than or equal to about 0.15.

27. The method of claim 26 wherein said applied energy is heat and said tubing remains shrunken after cooling, whereby said needle shank and suture remain coupled after cooling.

28. A method for attaching a plurality of surgical needles to sutures to provide a plurality of detachable needle-suture devices comprising:
(a) providing a plurality of needles having a shank of reduced cross-section;

(b) placing a shrinkable tubing having an axial length in the range of from about 0.115 to about 0.160 inches around each reduced needle shank and a suture;

(c) applying energy to the shrinkable tubing to bring the tubing into engagement with each needle shank and suture to join the needle and suture; and, (d) controlling said energy application to provide a plurality of needle-suture devices meeting the pull-out force limits for removable needle attachment set forth in the United States Pharmacopeia and exhibiting a standard deviation in average pull-out force of less than or equal to about 0.15.

29. The method of claim 28 wherein said applied energy is heat and said tubing remains shrunken after cooling, whereby said needle shank and suture remain coupled after cooling.

30. A combined surgical needle-suture device which comprises:
(a) a needle having a shank of reduced cross-section;
(b) a suture; and
(c) a shrinkable tubing around said needle shank and a portion of said suture, a surface contact area defined between said shrinkable tubing and at least one of said needle shank and/or suture to provide a detachable needle-suture device, said surface contact area having a contact area in the range of about 0.001 to about 0.008 square inches.

31. The combined surgical needle-suture device of claim 30 wherein said contact area is in the range of from about 0.001 to about 0.006 square inches.

32. The combined surgical needle-suture device of claim 30 wherein the ratio of the axial length of the tubing to the effective axial length of the needle shank does not exceed about 3.5:1.

33. The combined surgical needle-suture device of claim 32 wherein said ratio is in the range of from about 1.6 to about 2.3.

34. The combined surgical needle-suture device of claim 30 wherein the ratio of the axial length of the tubing to the effective axial length of the suture tip is in the range of from about 1.8 to about 2.6.

35. The combined surgical needle-suture device of claim 30 wherein the axial length of the tubing is in the range of from about 0.115 to 0.160 inches.

36. The combined surgical needle-suture device of claim 30 wherein the axial length of the surface contact area is in the range of from about 0.04 to about 0.105 inches.

37. A combined surgical needle-suture device which comprises:
(a) a needle having a shank of reduced cross-section;
(b) a suture; and,
(c) a shrinkable tubing around said needle shank and a portion of said suture, a surface contact area defined between said shrinkable tubing and said suture to provide a detachable needle-suture device, said surface contact area related to suture size substantially as follows:

| Suture Size | Surface Contact Area (In$^2$) |
| --- | --- |
| 1 | .0023 to .0079 |
| 0 | .0020 to .0066 |
| 2/0 | .0017 to .0053 |
| 3/0 | .0011 to .0043 |
| 4/0 | .0008 to .0033 |
| 5/0 | .0006 to .0030 |

38. The combined surgical needle-suture device of claim 37 wherein the axial contact length of said tube and suture is in the range of from about 0.045 inches to about 0.105 inches.

39. The combined surgical needle-suture device of claim 37 wherein the tip of said suture has a diameter related to suture size substantially as follows:

| Suture Size | Suture Tip Diameter (In.) |
| --- | --- |
| 1 | .016 to .024 |
| 0 | .014 to .020 |
| 2/0 | .012 to .017 |
| 3/0 | .008 to .013 |
| 4/0 | .006 to .010 |
| 5/0 | .004 to .009 |

40. The combined surgical needle-suture device of claim 37 wherein the surface contact area is related to suture size substantially as follows:

| Suture Size | Surface Contact Area (In$^2$) |
| --- | --- |
| 1 | .0034 to .0062 |
| 0 | .0028 to .0054 |
| 2/0 | .0023 to .0048 |
| 3/0 | 0019 to .0034 |
| 4/0 | .0015 to .0028 |
| 5/0 | .0011 to .0025 |

41. The combined surgical needle-suture device of claim 40 wherein the axial contact length of said tube and suture is in the range of from about 0.060 to about 0.090 inches.

42. The combined surgical needle-suture device of claim 40 wherein the tip of said suture has a diameter related to suture size substantially as follows:

| Suture Size | Suture Tip Diameter (In.) |
| --- | --- |
| 1 | .018 to .022 |
| 0 | .015 to .019 |
| 2/0 | .012 to .016 |
| 3/0 | .010 to .012 |
| 4/0 | .008 to .010 |
| 5/0 | .006 to .009 |

43. The combined surgical needle-suture device of claim 40 where the ratio of the axial length of the tubing to the effective axial length of the needle shank is not less than about 1.2:1.

44. The combined surgical needle-suture device of claim 40 wherein said suture is a braided suture.

45. The combined surgical needle-suture device of claim 44 wherein said suture is tipped with cyanoacrylate.

46. The combined surgical needle-suture device of claim 37 wherein said suture is a monofilament suture.

47. The combined surgical needle-suture device of claim 37 wherein said suture is a braided suture.

48. A shrinkable tubing configured and dimensioned to engage a portion of a surgical suture and a needle to attach same in a substantially axial end-to-end relationship, the shrinkable tubing having a minimum expanded inner diameter and a maximum recovered inner diameter related to suture size substantially as follows:

| Tube No. | Suture Size | Min. Expanded Inner Diameter (In.) | Max. Recovered Inner Diameter (In.) |
|---|---|---|---|
| 1 | 3/0, 4/0 | .014 | .007 |
| 2 | 0, 2/0 | .018 | .012 |
| 3 | 1 | .025 | .016 |

49. A combined surgical needle-suture device which comprises:
(a) a needle having a shank of reduced cross-section;
(b) a suture; and,
(c) a shrinkable tubing configured and dimensioned to surround at least a portion of said needle shank and suture to attach same and provide a detachable needle-suture device, said needle shank, suture and tubing dimensions related to each other substantially as follows:

| Suture Size | Needle Shank Diameter (In.) | Tube Dimensions | |
|---|---|---|---|
| | | Min. Expanded Inner Diameter (In.) | Max. Recovered Inner Diameter (In.) |
| 3/0, 4/0 | .010 | .014 | .007 |
| 0, 2/0 | .016 | .018 | .012 |
| 1 | .020 | .025 | .016 |

50. The needle-suture combination of claim 49 wherein said tubing has a maximum recovered wall thickness substantially as follows:

| Suture Size | Maximum Recovered Wall Thickness (In.) |
|---|---|
| 3/0, 4/0 | .0055 |
| 0, 2/0 | .0065 |
| 1 | .0090 |

51. A plurality of detachable needle-suture combinations each comprising a size 0 braided synthetic absorbable suture joined to a needle, the plurality of needle-suture combinations meeting the pull-out force limits for removable needle attachment set forth in the United States Pharmacopeia and exhibiting a standard deviation in average pull-out force of less than or equal to about 0.15,
wherein the suture is joined to a needle having a reduced diameter shank by a heat shrinkable tubing surrounding at least a portion of the needle shank and a portion of the suture.

52. A plurality of detachable needle-suture combinations, each comprising a size 4/0 braided synthetic absorbable suture joined to a needle, the plurality of needle-suture combinations meeting the pull-out force limits for removable needle attachment set forth in the United States Pharmacopeia and exhibiting a standard deviation in average pull-out force of less than or equal to about 0.05,
wherein the suture is joined to a needle having a reduced diameter shank by a heat shrinkable tubing surrounding at least a portion of the needle shank and a portion of the suture.

53. A plurality of detachable needle-suture combinations, each comprising a size 0 monofilament polypropylene suture joined to a needle, the plurality of needle-suture combinations meeting the pull-out force limits for removable needle attachment set forth in the United States Pharmacopeia and exhibiting a standard deviation in average pull-out force of less than or equal to about 0.05,
wherein the suture is joined to a needle having a reduced diameter shank by a heat shrinkable tubing surrounding at least a portion of the needle shank and a portion of the suture.

54. A plurality of detachable needle-suture combinations, each comprising a size 2/0 monofilament polypropylene suture joined to a needle, the plurality of needle-suture combinations meeting the pull-out force limits for removable needle attachment set forth in the United States Pharmacopeia and exhibiting a standard deviation in average pull-out force of less than or equal to about 0.03,
wherein the suture is joined to a needle having a reduced diameter shank by a heat shrinkable tubing surrounding at least a portion of the needle shank and a portion of the suture.

55. A plurality of detachable needle-suture combinations, each comprising a size 2/0 braided nylon suture joined to a needle, the plurality of needle-suture combinations meeting the pull-out force limits for removable needle attachment set forth in the United States Pharmacopeia and exhibiting a standard deviation in average pull-out force of less than or equal to about 0.04,
wherein the suture is joined to a needle having a reduced diameter shank by a heat shrinkable tubing surrounding at least a portion of the needle shank and a portion of the suture.

56. A plurality of detachable needle-suture combinations, each comprising a size 3/0 braided nylon suture joined to a needle, the plurality of needle-suture combinations meeting the pull-out force limits for removable needle attachment set forth in the United States Pharmacopeia and exhibiting a standard deviation in average pull-out force of less than or equal to about 0.30,
wherein the suture is joined to a needle having a reduced diameter shank by a heat shrinkable tubing surrounding at least a portion of the needle shank and a portion of the suture.

57. A plurality of detachable needle-suture combinations, each comprising a size 0 braided nylon suture joined to a needle, the plurality of needle-suture combinations meeting the pull-out force limits for removable needle attachment set forth in the United States Pharmacopeia and exhibiting a standard deviation in average pull-out force of less than or equal to about 0.11,
wherein the suture is joined to a needle having a reduced diameter shank by a heat shrinkable tubing surrounding at least a portion of the needle shank and a portion of the suture.

* * * * *